United States Patent [19]

Woollam

[11] Patent Number: 4,808,827

[45] Date of Patent: Feb. 28, 1989

[54] METHOD AND APPARATUS FOR MONITORING THE CONCENTRATION OF AIRBORNE ACTINIDE PARTICLES

[75] Inventor: Paul B. Woollam, Dursley, United Kingdom

[73] Assignee: Central Electricity Generating Board, London, England

[21] Appl. No.: 934,668

[22] Filed: Nov. 24, 1986

[30] Foreign Application Priority Data

Nov. 25, 1985 [GB] United Kingdom ............... 8528989

[51] Int. Cl.$^4$ .......................... G01T 1/36; G01T 1/24
[52] U.S. Cl. .......................... 250/370.02; 250/370.06; 250/304; 250/435
[58] Field of Search ............... 250/370 A, 364, 432 R, 250/435, 304, 380, 370 B, 370 E

[56] References Cited

U.S. PATENT DOCUMENTS

| 2,892,091 | 6/1959 | Sawle | 250/435 |
| 4,286,155 | 8/1981 | Utting | 250/380 |
| 4,442,358 | 4/1984 | Kreiner | 250/435 |
| 4,607,165 | 8/1986 | Burghoffer | 250/435 |

OTHER PUBLICATIONS

Rusch et al, "The ZPR-9 Airbourne Plutonium Monitoring System", IEEE Trans. Nucl. Sci., NS-23 (1), pp. 690-693, Feb. 1976.
Kordas et al, "A Review of Measurement Techniques for Stack Monitoring of Long-Lived Alpha Emitters", IEEE Trans. Nucl. Sci., NS-26 (1), Feb. 1979, pp. 757-764.

Primary Examiner—Carolyn E. Fields
Attorney, Agent, or Firm—Willian Brinks Olds Hofer Gilson & Lione

[57] ABSTRACT

The permissable level of radioactivity due to airborne actinides is extremely low: the satisfactory discrimination of actinide emissions from other sources is, consequently, a problem. This specification discloses the combination of (a) selecting only the larger airborne particles, (b) measuring the activity of emissions at the energy characteristic of actinide decay of these particles and (c) decay analysis of the measurements to reject emissions which are characteristic of high energy processes but which have lost sufficient energy to fall within the measurement band.

28 Claims, 5 Drawing Sheets

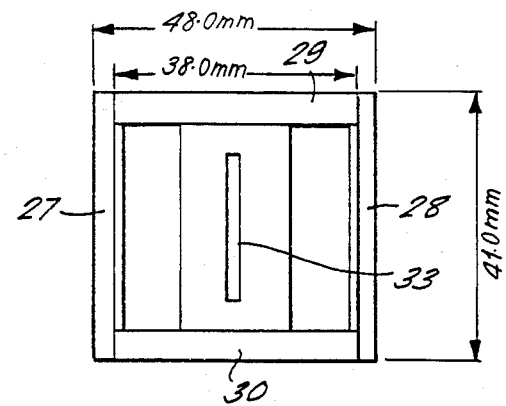
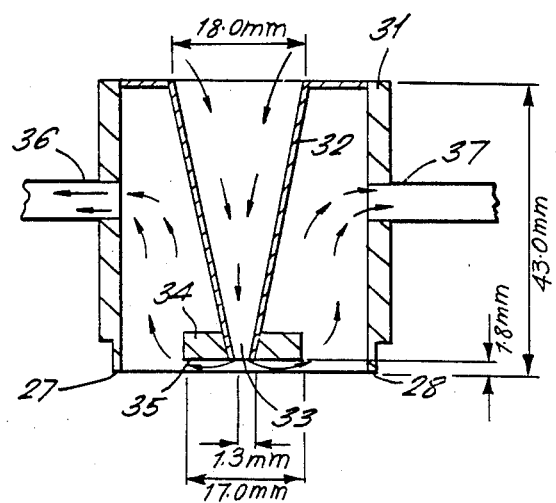

METHOD AND APPARATUS FOR MONITORING THE CONCENTRATION OF AIRBORNE ACTINIDE PARTICLES

TECHNICAL FIELD

The present invention is concerned with monitoring the concentration of airborne actinides.

BACKGROUND OF THE INVENTION

Adequate control over the concentration of radioactive particulate material in breathing air is essential in the responsible and acceptable operation of nuclear fuel facilities. Radioactive contamination of the air is sometimes caused by aerosols containing actinide bearing particles, typically a combination of one or more of the $\alpha$ emitting isotopes: $^{238}$Pu, $^{239}$Pu, $^{240}$Pu, $^{241}$Am, $^{242}$Cm and $^{244}$Cm, together with the $\beta$ emitting actinide $^{241}$Pu.

The classical method of monitoring airborne radioactivity is to sample the air, filter out any particulate matter in the air, and then monitor the radioactive emissions from the filter. The trouble with monitoring actinide radioactivity in the air is that the permissable radioactivity levels are so low as to be masked by the natural background airborne $\alpha$ radioactivity, particularly from the decay products (daughters) of radon gas. The radon daughters which typically interfere with $\alpha$ emission detection of actinides are the following: $^{218}$Po (RaA), $^{214}$Po (RaC'), $^{216}$Po (ThA), $^{212}$Bi (ThC) and $^{212}$Po (ThC'). The maximum permissable actinide radioactivity concentration for air (MPC$_a$) as laid down by International Commission on Radiological Protection (ICRP) is typically between 3 and 6 dpm m$^{-3}$ (1.4 to 2.8$\times$10$^{-12}$ uCi cm$^{-3}$), depending on the isotope mix. The safety rules of the Central Electricity Generating Board (CEGB) in England and Wales define a Contamination Zone Class CIII (into which persons entering must wear approved full face respiratory protection) as an area where, averaged over a period not exceeding 13 weeks, airborne radioactivity concentrations are expected to exceed one tenth of the ICRP recommended maximum (MPC$_a$) for a forty week occupational exposure. Accordingly, in order to monitor a region to ensure it remains below the lower limit requiring respiratory protection, the monitoring apparatus must be capable of sensitivities to the actinides of typically between 0.3 and 0.6 dpm m$^{-3}$. By comparison, under normal conditions the concentrations one metre above ground level of natural radioactivity resulting from $^{222}$Rn (radon) plus $^{220}$Rn (thoron) range from 400 to 4,000$\times$10$^{-13}$ uCi cm$^{-3}$. The above CEGB lower limit for which respiratory protection must be used is called the Derived Working Level (DWL).

Statistical uncertainties make it impossible to monitor the instantaneous radioactivity level and in practice average values over extended periods of time are determined. If the airborne actinide concentration is not to average above 1 DWL during a working shift to say 8 hours, this is equivalent to measuring that the actinide concentration does not exceed 8 DWL-hours by the end of an 8 hour shift.

The techniques for monitoring actinide concentration in the air which has been adopted previously in most cases is to sample the air and then wait 72 hours before monitoring the $\alpha$ emissions from the sample. The $\alpha$ emitting radon daughters from natural background radiation have relatively short half lives, typically a few minutes, compared to the half lives of the actinides (half a year to several thousand years). Accordingly the above technique permits the natural radon and thoron daughter products to decay to practical insignificance before monitoring the sample to detect the remaining $\alpha$ emissions which should be representative of actinides. This delay of 72 hours can, however, pose operational problems since additional precautions must be maintained in case there should be a relatively sudden increase in actinide concentration which would not be detected by previous methods for three days. Accordingly breathing protection must often be used even when, in reality, airborne radioactivity levels are in fact much lower than the lower limit for the zone requirements (e.g. CEGB Class CIII). Furthermore, existing techniques actually obtain an average of the contamination over an eight hour shift and provide the results of this monitoring only three days later. If an unexpectedly high count is in due course observed, it is often difficult to determine the particular part of the operation during the shift three days previously which might have been responsible.

There are various proposals in the prior art for actinide monitoring apparatus and methods which provide, at least at some extent, "on-line" monitoring. In "The ZPR-9 Airborne Plutonium Monitoring System", IEEE Transactions on Nuclear Science, Vol. NS-23, No. 1, February 1976, by Rusch, McDowell and Knapp, an on-line monitor is disclosed which samples the air but discriminates against solid particles which have less than a certain minimum aerodynamic size (1.5 microns). This separation is based on the observation that the radon and thoron daughter products are normally associated with dust particles which are generally substantially smaller than the actinide containing particles.

The apparatus described in this prior art article then provides some further rejection of remaining radon and thoron daughter activity in the collected sample by distinguishing between the characteristic energies of the resulting emissions. The described apparatus employs a silicon detector which provides an output pulse dependent on the energy of the detected $\alpha$ emission. In the described example the energy resolution of the detector is about 300 keV.

Separate scalers are arranged to count pulses from the detector in two different energy windows, one representing $\alpha$ energies between 5 and 5.4 MeV and the other representing energies between 5.5 and 7 MeV. In this way the count of pulses representing emissions having energies in the first window is a count primarily of $\alpha$ emissions from the decay of $^{239}$Pu, rejecting most of the $\alpha$ emissions from decay of the radon and thoron daughter products, which have energies in the range from 6 MeV up to nearly 9 MeV.

Because some $\alpha$ particles lose some of their energy before being detected by the silicon detector, a proportion of higher energy $\alpha$ particles are nevertheless detected in the low energy window and the described apparatus cancels these out by recording also the number of counts in the high energy window and subtracting a fixed proportion of these from the count in the lower energy window. Because the low energy window of the described apparatus extends only between 5 and 5.4 MeV, the apparatus measures primarily only the radioactivity resulting from $^{239}$Pu and $^{240}$Pu, which have characteristic energies in this range. The apparatus is not responsive to certain further actinides which can be important constituents of airborne radioactivity particularly resulting from the fuel cycle of thermal nuclear power stations.

Furthermore, the apparatus described in this prior art article has a sensitivity sufficient to enable it to be set to alarm if airborne plutonium concentrations exceed about $2\times10^{-11}$ $\mu$Ci-hr cm$^{-3}$ (10 RCG-hr using the notation of the publication). This corresponds to approximately 100 DWL-hr (using the notation referred to previously), which implies that an airborne radioactivity concentration in excess of 1DWL could exist throughout a 48 hour working week without causing the monitor in the prior art document to alarm. Clearly the monitor described in this publication would be unsuitable to meet the safety rules set down by the Central Electricity Generating Board.

Still further, the described apparatus is arranged to collect particulate matter from the air directly on a greased surface of the $\alpha$ emission detector. As a result the apparatus cannot be left unattended for an extended period of time since the detector must be cleaned and re-greased each morning.

A further prior art publication of interest is "A Review of Measurement Techniques for Stack Monitoring of Long Lived $\alpha$ Emitters", IEEE Transactions On Nuclear Science, Vol. NS-26, 757 (1979). This publication reviews various techniques for stack monitoring of long lived $\alpha$ emitters and refers briefly to the above described ZPR-9 monitoring system. An alternative arrangement for discriminating against small particles in the sampled air is described, constituting a two stage virtual impactor. The virtual impactor system deposits the larger size particles on a filter paper immediately in front of the detector, instead of directly on the detector face as described previously.

This second article then goes on to describe an alternative monitoring system called "The Transuranic Aerosol Measurement System (TAMS)". This system does not perform any particle separation by size in the sampled air. All particles in the sampled air are deposited on a section of a strip of filter paper. The filter paper extends between feed and take-up spools and when a sufficient sample is collected on a particular section of the paper strip, the strip is wound on to bring the sample into a detection chamber. The detection chamber is then sealed and evacuated before $\alpha$ emissions from the sample are monitored and counted. The evacuation of the detection chamber substantially improves the spectral resolution of the different energies of $\alpha$ emissions from the sample. In this way the various $\alpha$ emitters in the sample can be better distinguished from one another by their different characteristic energies, and in particular $\alpha$ emissions from actinides can be more readily distinguished from $\alpha$ emissions from background radon and thoron daughter products. The articles also refers to the possibility of "decay scheme analysis" to eliminate residual, natural $\alpha$ background which might not otherwise be rejected by the energy discrimination. In particular the $\alpha$ emissions from $^{218}$Po might be difficult since their characteristic energy is about 5.99 MeV which is close to the characteristic energies of certain actinides. The decay scheme analysis mentioned in the article would be based on the difference in half lives between the long lived $\alpha$ emitters (the actinides) and the relatively short half life of $^{218}$Po.

In the event, the article states that sufficient resolution is obtained simply from energy resolution so that decay analysis was not required or performed. The sensitivity of the system described in this second article enables it to measure a concentration of 0.25 DWL from a 60 minute sample with a fractional standard deviation of 18%. This is very much more sensitive than the ZPR-9 apparatus described previously but there are certain difficulties in using the described system.

The need to evacuate the detection chamber adds substantial complication to the apparatus. The evacuation requirement is crucial to the high energy resolution performance of the described device. However there is a tendency for particles to be detached from the filter paper during evacuation and to contaminate the face of the detector. Additionally, it is of critical importance that the filter medium used in the described system is of extremely high quality so as to prevent any substantial number of collected particles from penetrating into the medium. A very expensive filter medium is required to maintain good resolution and this would indicate a cost of operation of around £1,000 per month.

The described system is also particularly adapted for monitoring $\alpha$ emitters in stack effluents, positioned downstream of the stack's own filters. These stack filters are designed to remove particulate material from the effluent down to very small sizes with great efficiency. As a result a very large proportion of the dust particles on which radon and thoron daughter products may have aggregated have already been removed by these filters before the sampling point. The system would not operate with as much success in a different environment with the normal concentration and size range of dust particles and hence the normal radon and thoron background.

BRIEF SUMMARY OF THE INVENTION

The present invention sets out to provide a monitoring system for airborne actinides which has a sensitivity sufficient to monitor at below the DWL (as defined previously) and to provide a relatively fast response to a rise in radioactivity concentration which might result in safety levels being exceeded.

According to one aspect of the present invention, there is provided a method of monitoring the airborne radioactivity concentration represented by actinides, comprising the steps of drawing a sample stream of air from the region to be monitored, preferentially separating by size particles from the stream which are characteristic of actinide bearing particles from particles characteristic of the majority of natural dust particles and collecting said particles characteristic of actinide bearing particles onto the surface of a collection medium at a collecting position to provide a collected sample of particles, transferring the collection medium with said sample of particles collected thereon to a detecting position, detecting at the detecting position the relative energy of the radioactivity emissions from the collected sample on the collection medium, providing indications of the respective count rates of emissions detected having energies in each of a first energy window embracing the characteristic energies of actinide $\alpha$ emissions and excluding the characteristic energies of $\alpha$ emissions from $^{214}$Po (RaC') and a second energy window embracing said characteristic energies of $\alpha$ emissions from RaC' and excluding said characteristic energies of actinide $\alpha$ emissions, determining from said indications the variation with time of at least the count rate for said first energy window for the same collected sample, and calculating, from said count rate indications and said variation, a value for the count rate for α emissions from actinide bearing particles in the collected sample.

By employing in this method a combination of selection of particles by size, to exclude a majority of dust particles responsible for the natural radon and thoron background, α energy discrimination, to reject counts from remaining radon and thoron daughter products with characteristic energies outside the range occupied by actinide α emissions, and decay analysis to reject the contribution from radon daughter products having α energies within the actinide range, a composite method is provided which has the desired sensitivity as will become apparent later herein. Furthermore the described method is capable of responding to a full range of possible actinide particles since the characteristic energy of Rac' is 7.68 MeV whereas the highest characteristic energy of an actinide likely to be a problem with airborne actinide radioactivity is 6.11 MeV ($^{242}$Cm). It has been found that only two radon daughter products are responsible for the great majority of the background alpha radiation. These are the products RaA, which has a characteristic energy of about 6MeV, and the above referred Rac' with its characteristic energy of about 7.7 MeV. The energy resolution of the method of this invention enables the contribution to the overall count of the decay of Rac' to be substantially rejected. However, the first energy window of the method must embrace the characteristic energies of α emissions of RaA if it is to cover the full range of actinide emissions. The half life of RaA is 3.05 minutes whereas the half life of the shortest lived actinide ($^{242}$Cm) is 0.45 year. Thus for typical counting periods of from a few minutes to a few hours, the actinide concentration can be considered to remain substantially constant, whilst the concentration of RaA will reduce drastically as it decays. By monitoring the variations with time of the count rates in the two energy windows from the same collected sample, the contribution in the low energy window from RaA can be substantially eliminated from a knowledge of the expected rate of decay of RaA.

It should be appreciated that not all α emissions from a particular decay event in the sample will be detected in the detector with the characteristic energy of the decay. Although it may be assumed that an α emission of a particular decay event has initially the characteristic energy, the α particle will lose some of this energy before entering the detector. The most common and unavoidable cause of this loss of energy is due to the α particle having to penetrate through a thickness of its associated particle of matter, before reaching the detector. Accordingly, the proportion of particles detected with substantially less than the expected characteristic energy is primarily dependent on the range of sizes and densities of their associated particles of matter. The bigger the typical particle size or the more dense the particle, the greater is the loss of energy before entering the detector.

The effect of this in terms of energy resolution by the detector is that a proportion of particles having characteristic energies in the upper window are in fact detected with energies falling in the lower window. Thus the count in the lower energy window will include a number of counts which correspond to reduced energy α emissions from RaC'. The proportion of the total number of α emissions from Rac' which will be detected in the lower energy window is likely to be substantially constant for a particular apparatus and in a particular environment, with substantially consistent dust size. In order to correct for this spill-over of α emissions from Rac' which are detected in said first energy window, a predetermined portion of the count rate determined in said second energy window is subtracted from the count rate determined in said first energy window.

Then the α emissions from RaA are compensated for in the calculated actinide count rate value by analysis of the variation with time of the count rate determined in the first energy window, as corrected for said spill-over of α emissions from RaC'. In this way decay analysis is used to correct only for emissions from RaA, which has a predictable decay pattern which is unaffected by the concentration of other radon daughter products. By comparison the behaviour of Rac' is more complex, depending on the levels of RaA and also RaB ($^{214}$Pb).

A further important feature of the present invention is that the actinide particles separated from the air stream are collected onto the surface of the collection medium which is then itself transferred from the collection position to the detecting position. Collecting on the surface of the collecting medium avoids the need to use a filter paper and thus the danger of particles penetrating into the thickness of the filter paper. Instead an impervious collection medium is used and the particles may be imparted onto the surface or collected on the surface with the assistance of a tacky layer on the surface.

In a preferred arrangement the particles are preferentially separated by size using an inertial impactor arranged to collect said particles characteristic of actinide bearing particles by impaction onto the surface of the collecting medium at said collection position, without substantial penetration of the particles into the collecting medium. It is important that the collection medium has sufficient surface hardness or strength to prevent the impacting particles from penetrating into the surface.

Preferably, air from the region to be monitored is sampled continuously by presenting successive clean surface regions of collecting medium for collection of separated particles thereon during respective collecting periods, and transferring said surface region to the detecting position after said successive collecting periods.

The method preferably further includes the steps of calculating a count value for each successive collected sample corresponding to α emissions from actinide bearing particles in the sample, keeping an aggregate count during a normal working shift period of the total of calculated count values from successive collected samples since the start of the shift period, and producing an alarm signal if the aggregate exceeds a predetermined maximum value during the shift period. By this technique, the method can respond relatively quickly to a sudden rise in actinide concentration which might, for example, result in the count value exceeding the predetermined maximum value during a single sampling period. The event then results in an alarm within about one sampling period following the event, which may be a period substantially shorter than the normal working shift (typically eight hours). On the other hand, by accumulating successive count values to produce an aggregate count, the aggregate count itself can be used to provide a measure of the average actinide concentration during the shift to a substantially greater statistical accuracy than any one count value during a single sampling period.

In another aspect of the invention, there is provided apparatus for monitoring the airborne radioactivity concentration represented by actinide bearing particles, comprising means to draw a sample stream of air from the region to be monitored, a collection medium at a collecting position, means to separate preferentially by size particles from the stream from particles characteristic of the majority of natural dust particles and to collect said particles characteristic of actinide bearing particles onto the surface of said collecting medium at the collecting position to provide a collected sample of particles, a detector for detecting and providing indications of the relative energy of $\alpha$ radioactive emissions from a sample at a detecting position, means to transfer the collection medium with said sample of particles thereon from the collecting position to the detecting position, and counting and calculating means responsive to said indications from the detector and arranged (a) to provide indications of the respective count rates of emissions detected having energies in each of a first energy window embracing the characteristic energies of actinide $\alpha$ emissions and excluding the characteristic energies of $\alpha$ emissions from $^{214}$Po (RaC') and a second energy window embracing said characteristic energies of $\alpha$ emissions from Rac' and excluding said characteristic energies of actinide $\alpha$ emissions.

(b) to determine from said count rate indications the variation with time of at least the count rate for said first energy window for the same collected sample, and (c) to calculate from said count rate indications and said variation, a value for the count rate for $\alpha$ emissions from actinide bearing particles in the collected sample.

Preferably said means to separate and collect onto the surface of the collecting medium comprises an inertial impactor arranged to separate by size and impact said particles characteristic of actinide bearing particles onto said surface. Preferably, said collecting medium is substantially impermeable to air. The surface of said collecting medium should be sufficiently hard to prevent particles impacted thereon from penetrating substantially into the medium. Conveniently, the collecting medium is paper having a glazed surface.

The collecting medium may include a thin layer of a sticky material provided on the surface of the paper to ensure particles impacting the surface become attached thereto.

In a preferred embodiment, the collecting medium is formed as an elongate web of material extending parallel to the direction of transfer from the collecting position to the detecting position and said means to transfer is arranged to move the web lengthwise. Clamp means may be included operable to clamp respective portions of the web in the collecting and detecting positions and to release said portions to permit the web to move when the portion thereof carrying the sample collected at the collecting position is transferred to the detecting position. In this way not only is the collecting medium positively clamped in position for impaction thereon of particles from the inertial impactor, but also the previously collected sample is clamped firmly against the detector to minimise any energy loss of $\alpha$ emissions before they are detected.

The apparatus preferably includes a supply roll of said web material from which the material is drawn during transfers of successive collected samples from the collecting position to the detecting position, said means to transfer including a take-up spool for the web, a motor to drive the take-up spool to draw the web from the supply roll during said transfers and means controlling the motor to stop drawing further web material for the respective transfer once a length corresponding to the distance between said collecting and detecting positions has been drawn from the supply roll. Said means controlling the motor may include a tracking wheel engaging the web, to be rotated by movement of the web during a transfer, and means responsive to the tracking wheel rotating during a transfer through a predetermined angle corresponding to said length of web to stop the motor.

In a preferred example, the circumference of the tracking wheel is equal to an integral number of said lengths.

Preferably the detector is a silicon detector having a detection face. There may be clamp means operable to hold said sample of particles on the collection medium at a predetermined proximity to but not touching said detection face for detection of emissions from the sample.

Said counting and calculating means are preferably arranged such that said first energy window embraces the characteristic energies of $\alpha$ emissions from $^{218}$Po (RaA). Then said counting and calculating means may be arranged to correct, in said calculated actinide count rate value, for spill-over of $\alpha$ emissions from Rac' which are detected in said first energy window, by subtracting a predetermined proportion of the count rate determined in the second energy window from the count rate determined in the first energy window. Said counting and calculating means may further be arranged to compensate in said calculated actinide count rate value, for the emissions from RaA by analysing the variation with time of the count rate determined in the first energy window, as corrected for said spill-over of $\alpha$ emissions from RaC'.

In one embodiment, the apparatus is arranged to provide continuous sampling of air from the region to be monitored, successive clean surface regions of collecting medium being presented to said means to separate and collect, for collection thereon of said particles during respective collecting periods, and said means to transfer being operative to transfer said surface region to the detecting position after said successive collecting periods. Then said means to transfer may be operative to hold said surface region at the detecting position for the duration of the collecting period for the next successive surface region at the collecting position. The successive collecting periods may be of the same duration which may be less than the normal working shift period (typically eight hours). Each said collecting period may be less than one hour.

Said counting and calculating means may be arranged to calculate a count value for each successive collected sample corresponding to $\alpha$ emissions from actinide bearing particles in the sample, and to keep an aggregate count during a normal working shift period of the total of calculated count values from successive collected samples since the start of the shift period, and the apparatus may then include alarm means responsive to the aggregate count to produce an alarm signal if the aggregate count exceeds a predetermined maximum value during a shift period.

BRIEF DESCRIPTION OF THE DRAWINGS

An example of the present invention will now be described with reference to the accompanying drawings in which:

FIG. 3 is a detailed view of the impactor from beneath;

FIG. 4 is a detailed cross sectional view in elevation of the impactor;

DETAILED DESCRIPTION

Figure 1:
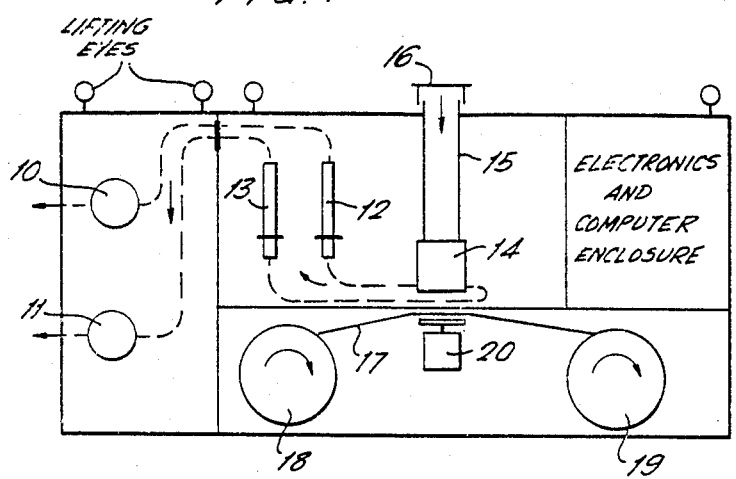
FIG. 1 is a schematic diagram of apparatus for monitoring the airborne radioactivity concentration of actinide bearing particles embodying the present invention.

Referring firstly to FIG. 1, air from the region to be monitored by the apparatus is sampled by means of a pair of pumps 10 and 11. The pumps 10 and 11 are constant displacement pumps of high volume flow rate. Examples of appropriate pumps are the carbon vane pumps of Rotheroe and Mitchell which each have a volume floor rate of 100 liters per minute. It will be appreciated that the described apparatus is intended for monitoring extremely low airborne radioactivity concentrations corresponding to extremely low volume concentrations of actinide bearing particles in the region being monitored. Thus, relatively high volumes of air must be sampled from the region if a statistically valid sample is to be obtained over the sampling period. For example, for an airborne activity concentration at the CEGB DWL defined above, it would take 17 minutes for a sampler running at 60 liters per minute to sample one cubic meter of air, thus allowing a standard deviation in the statistically expected number of actinide bearing particles collected from a typical nuclear fuel facility to be reduced to 32%. The resulting sample if then counted in a typical detector system with 33% efficiency would on average require almost 10 minutes to acquire just one actinide α count and 100 minutes of counting to achieve a 32% uncertainty on the validity of the count from counting statistics. This demonstrates the basic difficulty in determining the concentration of actinide in an aerosol at the very low DWL, over a short time period. There are fundamental statistical limitations. However, increasing the volume flow rate of air sampled improves the statistical validity of the number of particles collected.

In FIG. 1, the air is drawn by the pumps 10 and 11 through flow meters 12 and 13 from an inertial impactor contained in a head assembly 14. The design of the inertial impactor will be described in more detail later herein. The air sucked through the impactor is drawn along an earthed, metallic inlet tube 15 from an air inlet 16.

Figure 2:
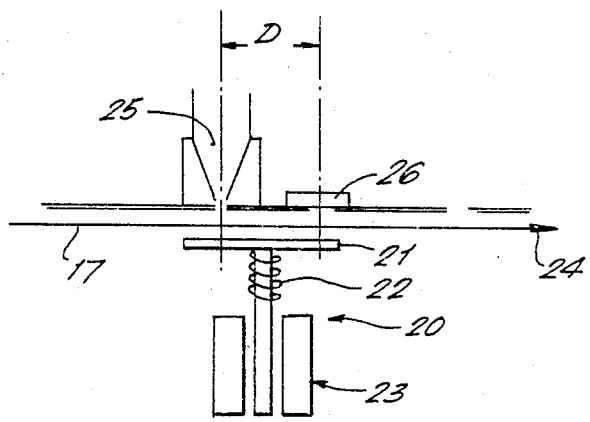
FIG. 2 is a schematic representation showing more detail of the impactor and detector head of FIG. 1.

FIG. 2 is a schematic view of the impactor and detector head assembly in greater detail. Referring to FIGS. 1 and 2, a paper tape 17 extends from a supply roll 18 to a take-up spool 19. A breech clamp assembly 20 has a pressure plate 21 arranged to engage an undersurface of a length of the paper tape 17 and securely press this portion of the tape against the impactor and detector head assembly 14. A compression spring 22 exerts the necessary clamping pressure on the plate 21. When pressed against the assembly 14, the paper tape 17 is located at a predetermined close proximity to, but not touching, the face of the detector. An electromagnetic coil 23 can be energised to retract the clamping plate 21 thereby allowing free movement of the paper tape when the tape is wound on in the direction of arrow 24 as will be explained later. The impactor head assembly 14 contains an inertial impactor jet 25 and a detector 26 which are spaced apart in the direction of movement of the paper tape by a distance D. The impactor jet 25 is designed and arranged to separate particles greater than a predetermined aerodynamic diameter in the incoming sample air stream from smaller diameter particles. These separated larger particles become impacted on the surface of the paper tape 17 immediately under the jet 25. After a predetermined sampling time, typically 30 minutes, during which the breech clamp assembly presses the paper tape firmly against the impactor, the breech clamp is released, freeing the paper tape and the paper tape is moved forward in the direction of arrow 24 by a distance D. Reengagement of the breech clamp assembly then presents the collected sample directly to the detector 26 for counting of α emissions therefrom.

The apparatus is designed so that the inertial impactor jet 25 is effective to separate out and collect by impaction on the surface of the paper tape 17 particles having aerodynamic diameters of the size of the large majority of actinide bearing particles likely to be airborne. On the other hand the design is arranged to discriminate against smaller particles in the sampled air stream including the majority of natural dust particles. Essentially, the gas flow in which particles are suspended is made to turn sharply with the result that heavier particles with high inertia continue in their original direction to impact on the surface of the paper, while lighter particles follow the gas stream lines and escape.

FIGS. 3 and 4 illustrate the design of the inertial impactor jet and give suitable dimensions which, for a gas flow rate of 200 liters per minute, result in 90% of particles of aerodynamic diameter 1 micron impacting on the collection surface, whereas only 10% of particles of 0.6 microns aerodynamic diameter are impacted.

FIG. 3 is an underneath plan view of the impactor jet and FIG. 4 is a cross sectional view in elevation looking along the direction of transport of the paper tape. When a sample is being collected, the clamping plate 21 of the breech clamp assembly presses the paper tape 17 firmly against the bottom edges 27, 28, 29 and 30 of an outer jacket 31 of the impactor jet. Air drawn from the region being monitored enters a funnel 32 which depends downwardly from an upper end of the outer jacket 31. The lower end of the funnel 32 forms a slot 33. The opening of the slot 33 is displaced slightly above the surface of the paper tape 17 and is surrounded by a flange 34 forming a jet face 35 spaced parallel to the paper tape 17. Suction ports 36 and 37 are provided in the external jacket 31 on opposite sides of the slot 33, connected to the respective air pumps 10 and 11. As can be seen, air is drawn by pumps down through the funnel 32, to emerge at the slot 33, to escape between the jet face 35 and the upper surface of the paper tape 17 into the area defined by the external jacket 31. As a result, the air emerging from the slot 33 is made to turn sharply to each side perpendicular to the length of the slot before emerging into the interior of the jacket 31. Heavier particles entrained in the air emerging from the slot 33 do not turn in the air stream sufficiently sharply and impact on the surface of the paper tape 17. The smaller particles do not impact the tape and escape with the air.

In order to separate out particles of the sizes mentioned above, and for an air flow rate of 200 liters per minute, the width of the slot 33 should be 1.3±0.1 mm, the spacing of the jet face to the paper should be 1.8±0.2 mm and the width of the jet face 35 perpendicular to the slot direction should be 17±0.3 mm. In the illustrated example, the length of the slot is 20±0.2 mm.

It is important that particles impacting on the surface of the paper tape 17 do not penetrate the surface. Accordingly, the paper used is good quality paper with a glazed surface. A strip about 1cm wide in the centre of the paper tape along its length is coated with a tacky chemical to ensure that particles impacting on the paper adhere to the paper and are not blown off again. It should be noted that the orientation of the slot 33 of the impactor jet illustrated in FIGS. 3 and 4 is along the length of the paper tape and the 1 cm strip of tacky chemical should lie centrally under the slot 33 with about 0.5 cm extending on each side of the centre line of the slot. A suitable tacky chemical is that obtainable from Tak Chemicals.

Figure 5:
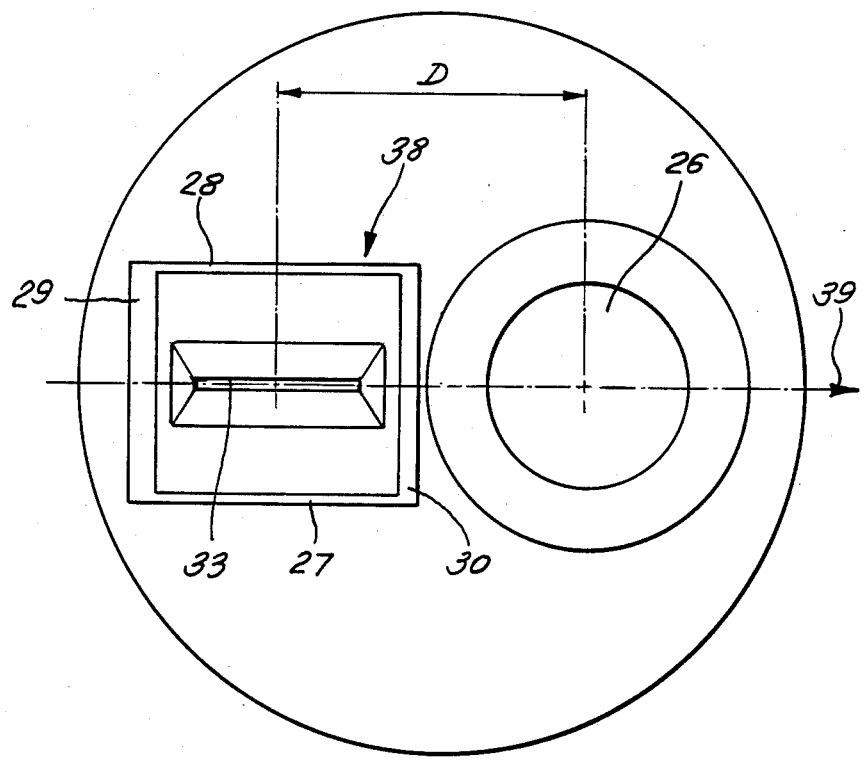
FIG. 5 is a view from beneath of the combined impactor and detector head.

FIG. 5 is an underneath plan view of the combined impactor and detector assembly, showing the impactor head at 38 with its slot 33 aligned with the direction 39 of transport of the paper tape. The detector 26 is mounted immediately adjacent to the impactor head 38 just downstream in the direction of paper tape transport. The detector 26 is a silicon surface barrier detector having a detecting surface with a diameter slightly greater (24 mm) than the length of the slot 33. The detector is formed of a silicon slice of thickness 100 micron and is capable of producing pulses representative of detected emissions which can resolve the energy of the particles within 30 keV Full Width at Half Maximum (FWHM) at room temperature. Both the impactor head 38 and the detector 26 are mounted in a mounting plate 40 so that the plane of the front of the mount of the detector 26 and also the lower edges 27, 28, 29 and 30 of the outer cavity 31 of the impactor head are flush with the lower surface of the mounting plate 40. The detecting surface itself of the detector 26 is set back a small amount from the surface at plate 40, to define the proximity at which the tape is clamped by the breach clamp.

All the surfaces of the edges 29 and 30 together with the mounting plate surrounding the detector 26 should be coated with polytetrafluoroethylene (PTFE) to prevent the tacky paper from sticking.

Figure 6:
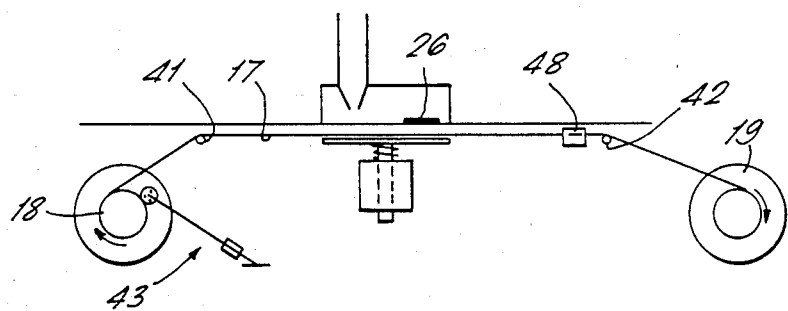
FIG. 6 is a schematic representation of the collection paper transport system used in the apparatus.
Figure 7:
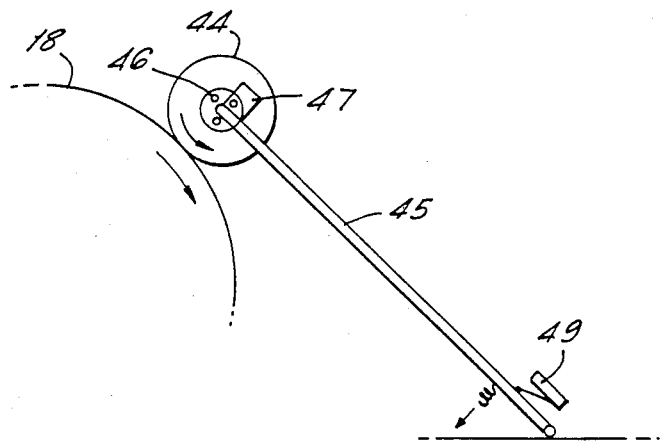
FIG. 7 is a detailed diagrammatic representation of the paper tape feed sensor from the transport system of FIG. 6.

FIGS. 6 and 7 illustrate the paper tape transport mechanism in more detail. As mentioned previously, the paper tape extends from a feed roll 18 to a take-up spool 19. The take-up spool 19 is driven by a synchronous motor to draw additional tape from the feel roll 18 when moving a collected sample the distance D from beneath the impactor head to beneath the detector. Paper tape guides 41 and 42 are arranged so that the paper tape extends naturally when the breech clamp is withdrawn as shown in the Figure, with a predetermined spacing from the impactor head and detector. During a sampling periods, the breech clamp deflects the paper against an accurately defined geometry relative to the impactor and detector head assembly and the predetermined spacing is sufficient to ensure that the paper tape strings away again when the breech clamp is withdrawn at the end of the sampling period.

At the end of a sampling period, the breech clamp is withdrawn and the synchronous motor energised to drive the paper take up spool 19. A paper travel sensor 43 monitors the amount of paper being drawn from the feed roll 18 and produces a signal stopping the motor after a length D has been supplied. The paper travel sensor 43 is shown in more detail in FIG. 7 and comprises a tracking wheel 44 mounted at the free end of a pivot arm 45 which is spring loaded to hold the wheel to track on the outer surface of the paper feed roll 18. The wheel 44 is formed of a plastic material and provided with a roughened edge to prevent slipping. The circumference of the tracking wheel 44 is equal to precisely three times the distance D between the centre of the impactor head 38 and the detector 26 (FIG. 5). A sense wheel 46 is mounted to rotate with the tracking wheel 44 and is machined with three holes equi-angularly spaced about the axis of the wheel. An infrared detector 47 responds to each of the holes in the wheel 46 by generating a pulse. The motor driving the take-up spool 19 is controlled by a computer system (not shown in FIGS. 6 and 7) and the computer system responds to the pulse on the sensor 47 by halting the motor. In this way the paper tape 17 is accurately moved the distance D after each sampling period.

Additional paper break and low paper sensors 48 and 49 provide respective inputs to the controlling computer to half further sampling in either eventuality.

Figure 8:
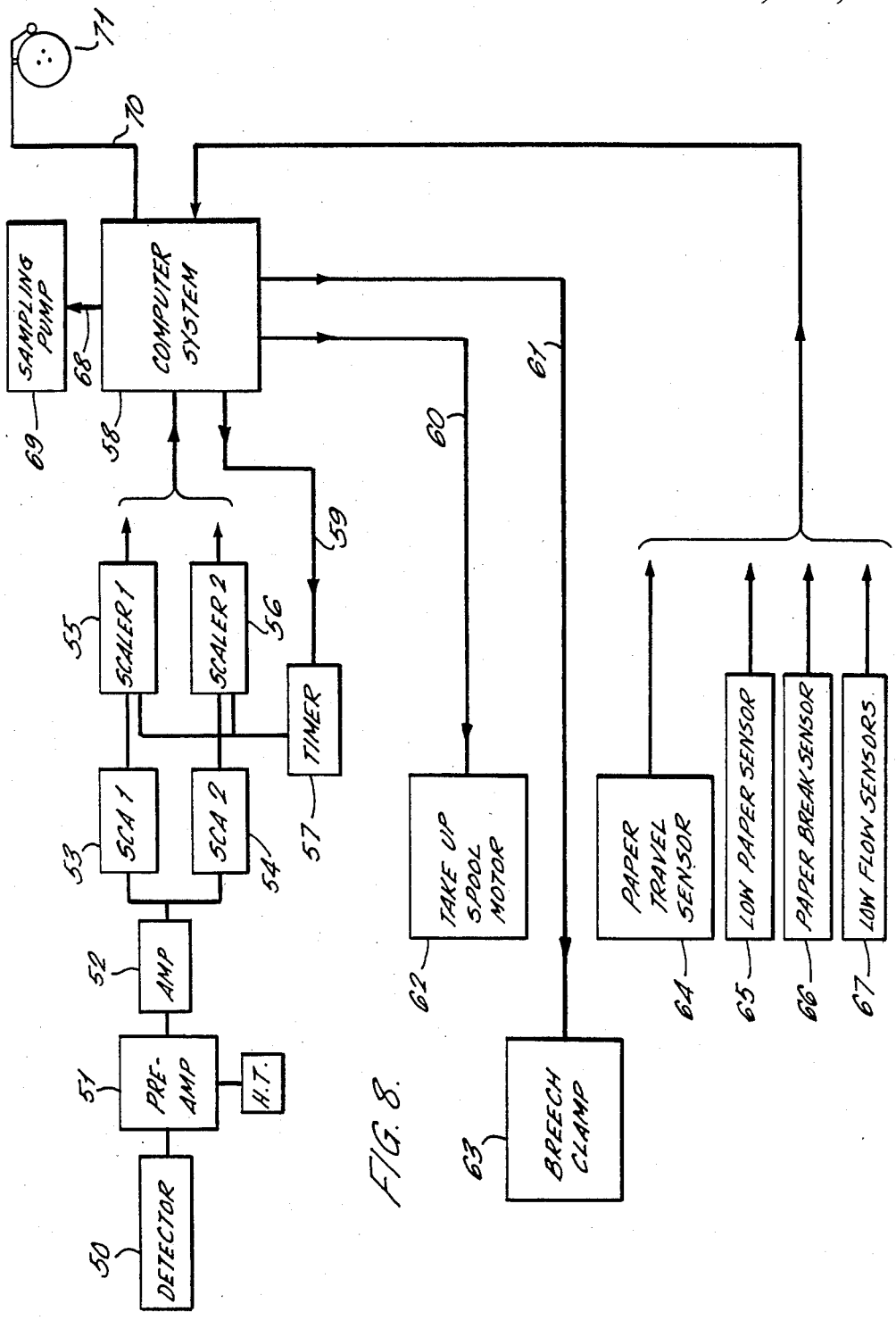
FIG. 8 is a block schematic diagram of the electronic counting, calculating and control system employed with the apparatus.

Referring now to FIG. 8, the electronics for analysing the pulses from the detector 26 and for controlling the previously described apparatus is illustrated in block diagrammatic form. The detector is shown in FIG. 8 at 50. The detector 50 produces pulses in response to a particles from the collected sample. The amplitude of the pulses from the detector 50 corresponds to the energy of the $\alpha$ particles detected. The pulses from the detector 50 are amplified in charge sensitive preamplifier 51 and further main amplifier 52. The gains of the amplifiers 51 and 52 are arranged to ensure that pulses from the detector 50 corresponding to detected $\alpha$ particles with energies between 2 MeV and 9 MeV are amplified without clipping.

The amplifier detector pulses are passed to two single channel analysers (SCA) 53 and 54. The single channel analysers 53 and 54 are arranged to select from the pulses from the amplifier 52 only those pulses having amplitudes within a predetermined range of amplitudes, corresponding to a predetermined range of energies of detected $\alpha$ particles. Accordingly each SCA defines a respective energy window and pulses corresponding to detected particles having energies within the respective energy window are passed by the SCA to a respective one of two scalers 55 and 56. The scalers 55 and 56 count the pulses passed by the SCAs 53 and 54 respectively in time periods set by timer 57 under the control of a computer system 58. The counts in the scalers 55 and 56 are also read in by the computer system 58 at the end of respective counting periods.

The computer system 58 analyses the counts in a manner which will be described in more detail later and also produces control signals on a line 59 for controlling the timer 57.

The computer system 58 is also programmed to control the paper tape feed mechanism, breech clamp mechanism and sampling pumps described previously. Output signals from the computer on lines 60, 61 and 68 comprise respectively signals to energise the take-up spool motor 62, to release the breech clamp 63 and to switch the sampling pumps 69 on and off. Signals from the paper travel sensor 64, the low paper sensor 65, the paper break sensor 66 and low flow sensors 67 on the flow meters 12 and 15 (FIG. 1) are all supplied to the computer system 58. The computer system 58 is programmed to respond to signals indicating low paper, paper break or low flow by halting further operation of the apparatus and raising an alarm.

The computer system 58 defines the sampling periods during normal operation of the apparatus and at the end of the sampling period, generates signals on lines 61 and 68 to release the breech clamp and turn off the pumps, and a signal on line 60 to energise the take-up spool motor to transport the paper tape through the distance D. The paper travel sensor 64 provides an indication once the paper tape has moved the distance D and the computer system 58 reacts by de-energising the motor, reapplying the breech clamp and turning off the pumps.

The SCAs 53 and 54 together with the computer system 58 are arranged to provide both energy analysis and decay analysis of the detected emissions from each collected sample. In the event of high actinide levels being detected the computer system generates a signal on line 70 to activate an alarm 71.

The apparatus is designed to detect the airborne radioactivity concentration resulting from the presence of actinide bearing particles in the air. The table below lists the most important actinide isotopes arising in the thermal nuclear power fuel cycle.

| Isotope | Halflife (y) | Alpha Energy (MeV) | MPC$_a$* ($\mu$Ci cm$^{-3}$) |
|---|---|---|---|
| $^{238}$Pu | 86 | 5.50, 5.46 | $2 \times 10^{-12}$ |
| $^{239}$Pu | 24,400 | 5.15, 5.13, 5.10 | $2 \times 10^{-12}$ |
| $^{240}$Pu | 6,580 | 5.17, 5.12 | $2 \times 10^{-12}$ |
| $^{241}$Pu | 14.9 | None | $9 \times 10^{-11}$ |
| $^{241}$Am | 458 | 5.48, 5.44, 5.39 | $6 \times 10^{-12}$ |
| $^{242}$Cm | 0.45 | 6.11, 6.07 | $1 \times 10^{-10}$ |
| $^{244}$Cm | 18.1 | 5.80, 5.76 | $9 \times 10^{-12}$ |

*Maximum permissible concentration in air for 40 h weeks (ICRP, 1959)

The above table shows that $\alpha$ emissions from these actinide isotopes have energies ranging from about 5 MeV to about 6.25 MeV. The background airborne radiation results from the $\alpha$ decay of radon and thoron and their daughter products. However, measurements of the $\alpha$ energy spectra of natural background airborne radioactivity have demonstrated that the only two significant sources of background are the radon daughter RaA and RaC'. The characteristic energies of $\alpha$ emissions from RaA and Rac' are 5.99 MeV and 7.68 MeV respectively.

It can be seen therefor that the characteristic energy of background $\alpha$ emissions from RaA fall within the band of energies of actinide $\alpha$ emissions.

The SCAs 53 and 54 shown in FIG. 8 are set up to provide a first, lower energy window accepting pulses representing detected alphas having energies between a lower level set above any $\beta$ energies from fission product decay (say about 3 MeV) and an upper level set just above the characteristic $\alpha$ energy of $^{242}$Cm (say about 6.3 MeV). The second SCA 54 is set to define an upper energy window having a lower level coincident with the upper level of SCA 53 (6.3 MeV) and an upper level set above the characteristic energy for Rac' (say 8 MeV).

The scalers 55 and 56 then count the pulses passed by the SCAs 53 and 54 in these two respective energy windows. It can be seen that the scaler 55 will provide a count which tends to reject particles from the decay of RaC'. However the count in scaler 55 still includes a proportion of $\alpha$ emissions from the decaying of RaA.

Furthermore, not all the $\alpha$ emissions detected by detector 50 from decay of Rac' are detected to have the characteristic energy (7.68 MeV). Some of the particles from decay of Rac' will have lost some energy before entering the detector. This can be observed as a low energy tail on the peak corresponding to the characteristic energy for Rac' in the $\alpha$ energy spectrum. $\alpha$ particles may lose some energy before being detected in the detector by having to travel through some thickness of a particle of matter before entering the detector, or else though a significant distance in air. The apparatus of the present invention is designed to minimise any energy loss in air by ensuring that the collected sample of particulate matter is pressed by the breech clamp into a defined geometry as close as possible to the face of the detector. However the collected sample is not brought into contact with the detector face to avoid contaminating or damaging the detector. The amount of particulate matter itself through which $\alpha$ particles travel is generally dependent on the size distribution of the particles of matter and will normally be substantially constant in a particular environment.

The result of the low energy tail of the Rac' peak in the $\alpha$ energy spectrum is that the count in scaler 55 will include some $\alpha$ emissions from RaC'. However in a particular set-up, i.e. with the apparatus operating to monitor the same region, the proportion of RaC'$\alpha$ emissions which are detected in the lower energy window compared to the counts in the upper energy window remains substantially constant. In tests with the present apparatus, the fraction of the upper energy window counts tailing into the lower energy window was determined to be 0.054.

Accordingly, the contribution to the count in the lower energy window from the tail of Rac' counts in the upper energy window can be reduced by subtracting from the lower energy window count a fixed fraction of the counts in the upper energy window. Ideally the fraction to be deducted would be precisely that found to represent the fractional distribution of the counts in the absence of any actinide contribution. However, in fact a lower fraction must be used to reduce the statistical chance of over-compensating in the lower energy window and therefore disguising the true actinide count. The computer system 58 is thus arranged to compensate in the count in scaler 55 for any low energy Rac' contribution by subtracting a predetermined fraction of the counts in scaler 56.

In order to distinguish and reject the contribution in scaler 55 of $\alpha$ emissions from decay of RaA the fact is utilised that RaA has a half life of about 3.05 minutes, whereas actinides have half lives measured in months and years. Accordingly the activity representative of actinides in a collected sample is likely to remain substantially constant during the counting period after the sample has been collected, whereas the activity representative of RaA in the sample will decay rapidly.

In order to avoid the need to delay counting emissions from the sample until RaA should have decayed into insignificance, the predictable rate of decay of RaA is used by the computer system 58 to cancel the RaA contribution.

The apparatus operates by first collecting a sample of particles on the paper tape by impaction. A sampling period is typically set at about 30 minutes. At the end of a sampling period, the paper tape is transported to bring the collected sample to the detector 26. Whilst the detector 26 is monitoring α emissions from the collected sample, a further sample is being collected on a fresh part of the paper tape. Accordingly it is convenient for the counting period during which α emissions from the collected sample are being counted to be the same as the collecting period during which each successive sample is collected.

In order to enable the contribution to the count in scaler 55 of RaA to be rejected by decay analysis, the timer 57 is controlled by the computer system 58 to reset the scalers 55 and 56 both at the beginning of a fresh sampling period, i.e. when the previously collected sample is first presented to the detector, and also once during the course of the sampling period. The computer system 58 reads the counts in the scalers 55 and 56 before each reset. Accordingly for each collected sample, the computer system 58 acquires the counts from scalers 55 and 56 for each of two successive time periods ($t_1$ and $t_2$).

It can be seen that the number of counts accumulated in time t in the lower energy window by scaler 55, α, can be represented for each of the two time periods $t_1$ and $t_2$ as follows:

$$\alpha_1 = A_1 + f\beta_1 + P_1 + B_1$$

$$\alpha_2 = A_2 + f\beta_2 + P_2 + B_2$$

The subscripts denote the time period. The count contribution from RaA decays is represented as A, the contribution from plutonium and other actinide decays, P, from the relatively constant background sources of cosmic rays etc, B, and from the low energy tail of the Rac' peak in the upper energy window, $f\beta$ where $\beta$ is the count in the respective time t in the high energy window and f is the fraction split into the low energy window.

Over a short time period (30 minutes or so) we may assume the long half life actinide count rate and the background count rate to be constant, the latter being determined, together with f, in the system calibration. The ratio of the total counts from RaA in the two time periods can be readily calculated from the decay constant for RaA. If the ratio of the two time periods $t_2/t_1 = r$ and the ratio of the integrated RaA counts in these time periods is R such that $A_2 = RA_1$, then also $P_2/P_1 = r$ and $B_2/B_1 = r$ and $$r\alpha_1 - \alpha_2 = (r-R)A_1 + f(R\beta_1 - \beta_2)$$

$$\alpha_1 + \alpha_2 = (1+R)A_1 + f(\beta_1 + \beta_2) + P_1 + P_2 + B_1 + B_2$$

Now $\alpha_1$, $\alpha_2$, $\beta_1$ and $\beta_2$ are all measured by the apparatus. The value of r allows R to be calculated from the known decay constant of RaA and, by operating the apparatus in situations where $P_1$ and $P_2$ are known to be zero, the spill fraction f can be measured. This fraction can vary marginally depending on the ambient particle size distribution of the airborne dust. If the sampling pumps of the apparatus are stopped, the background levels $B_1$ and $B_2$ can be measured for the particular location of the instrument. Substituting all these values into the first equation above allows $A_1$ to be determined. $A_1$ can then be substituted into the second equation above which allows the total actinide count $P_1 + P_2$ in the time $t_1 + t_2$ to be determined, thereby using the full statistical accuracy afforded by adding the upper and lower energy window counts for the two time periods.

It should be noted that this analysis does not rely on knowing the details of the potentially complex equilibrium and decay time dependence of RaC'.

On installing an instrument as described to monitor a particular region, the various calibration tests indicated above are first performed to set up the parameters in the computer system 58 to perform the above described calculations. As a result the computer system 58 operates to produce a count value at the end of each sampling period which represents the counts from actinide bearing particles in the previously collected sample with a high level of rejection of counts from natural background airborne radioactivity. As mentioned previously, the fundamental criterion (as employed by the C.E.G.B) for monitoring the potential hazard of airborne actinide radioactivity is that the instaneous activity level, (e.g. measured as decays per minute for each cubic meter of air) should not on average exceed the DWL over a period not exceeding 13 weeks. The averaging is implicit in the fact that the instantaneous airborne concentration levels are so low as to make it impossible to obtain a statistically significant sample of the re.g.ion being monitored in a very short response time of a few minutes. Furthermore, even if a statistically valid sample of the air could be taken in such a short time, the resulting radioactivity of the collected sample would still be so low that counting would have to be continued for an extended period to reduce the statistical uncertainty of the counting process.

The described apparatus can provide both a relatively fast response to sudden increases in radioactivity concentration, and also enables statistically valid measures to be made of the actinide activity level at very low levels below 1 DWL by averaging over an extended period of time, typically one working shift of eight hours.

The lower limit of detection of the described apparatus was assessed by operating the monitoring system to sample and count over successive 30 minute periods with the counting of each sample being divided into two intervals from 0 to 6 minutes and from 6 to 30 minutes. The system was operated continuously for a period of 45 days in an area expected to be completely clear of airborne actinide contamination. Evaluation of the equations above for the counts in the two energy windows for the two intervals in each 30 minute time period gives a total actinide count in each 30 minute period as:

$$P = -0.48\alpha_1 + 1.37\alpha_2 + f(0.48\alpha_1 - 1.37\alpha_2) - B.$$

The spill fraction f was taken to be 0.03, deliberately lower than the measured fraction 0.054.

The computer system 58 was programmed to perform this calculation on the count values from the scalers 55 and 56 to derive a calculated count for actinide particles for each sample. The resulting counts for successive samples at 30 minute intervals, were then aggregated in the computer to produce an average value of radioactive concentration over an eight hour shift. Over the 45 day period there were 134 eight hour shifts. The apparent actinide concentration calculated in this way for the 134 shifts showed concentration values ranging from 0 or slightly negative, up to about 0.3 dpm m$^{-3}$. Plotting time various values as a histogram demonstrated a peak at around 0.04 dpm m$^{-3}$, with about 7% of the total number of recorded values greater than 0.15 dpm m$^{-3}$, and a further 7% showing negative values.

Because the spill fraction f was taken as 0.03 instead of 0.054, not quite enough of the lower energy tail of Rac' is removed from the counts in the lower energy window. Hence the apparent actinide count is enhanced. If the correct spill factor were used in the calculations, the peak of the distribution of the calculated values would move from 0.04 to 0 and many of the individual higher level calculated values would be reduced markedly since they tend to be associated with high Rac' levels. However, the system would then record a relatively high number of shifts with an apparently negative actinide concentration, this negative value arising purely out of the counting statistics. Accordingly a selection of the value f at 0.03 is thought preferable to allow a greater than 95% confidence that the spilled Rac' count has not been over estimated, and hence that the actinide count is not underestimated.

It can be seen, therefore, that the system can measure an actinide activity concentration over an eight hour shift down to about 0.04 dpm m$^{-3}$ (which is 0.08 DWL for a typical isotope mix or $8 \times 10^{-3}$ of the ICRP recommended maximum) with a standard deviation, due to counting statistics, of 0.015 dpm m$^{-3}$.

Thus, the actinide monitor described has typically a practical, shift averaged sensitivity of less than 0.7 DWL-hour to actinide aerosols in the presence of natural airborne $\alpha$ activity. Furthermore, the monitor is capable of producing an alarm within an hour of a sudden rise in activity.

In order to avoid a high probability of false alarm, the instrument would normally be set to alarm if the aggregate count exceeded about 6 DWL-hour in an eight hour shift. This would result in virtually zero probability of a false alarm over a 45 day period.

It is unlikely that the system would fail to respond to an airborne concentration rising in access of 8 DWL-hour. At higher concentrations, the counts in the lower energy window are relatively higher thereby improving the counting statistics.

In summary, the instrument would typically be operated to monitor a particular working region on a shift by shift basis. The monitor would take a sample of the air during successive 30 minute periods and count that sample during the following 30 minute period. The aggregate calculated actinide count during the course of the shift is kept and if this aggregate count exceeds the predetermined level set for the entire shift, an alarm is produced. The system can be set to alarm at concentrations below 1 DWL averaged over an eight hour shift and furthermore can respond within an hour to a sudden increase in concentrations.

Meanwhile, the individual actinide counts for each successive 30 minute period can be stored for subsequent analysis of radioactivity arisings during each part of a complex operation.

I claim:

1. A method of monitoring the airborne radioactivity concentration represented by actinides, comprising the steps of drawing a sample stream of air from the region to be monitored, preferentially separating by size particles from the stream which are characteristic of actinide bearing particles from particles characteristic of the majority of natural dust particles and collecting said particles characteristic of actinide bearing particles onto the surface of a collection medium at a collecting position to provide a collected sample of particles, transferring the collection medium with said sample of particles collected thereon to a detecting position, detecting at the detecting position the relative energy of the $\alpha$ radioactive emissions from the collected sample on the collection medium, providing indications of the respective count rates of emissions detected having energies in each of a first energy window embracing the characteristic energies of actinide $\alpha$ emissions and excluding the characteristic energies of $\alpha$ emissions from $^{214}$Po (RaC') and a second energy window embracing said characteristic energies of $\alpha$ emissions from Rac' and excluding said characteristic energies of actinide $\alpha$ emissions, determining from said indications the variation with time of at least the respective count rate for the said first energy window for the same collected sample, and calculating, from said count rate indications and said variation, a value for the count rate for $\alpha$ emissions from actinide bearing particles in the collected sample.

2. A method as claimed in claim 1 wherein the particles are preferentially separated by size using an inertial impactor arranged to collect said particles characteristic of actinide bearing particles by impaction on to the surface of the collecting medium at said collecting position, without substantial penetration of the particles into the collecting medium.

3. A method as claimed in claim 1 wherein said first energy window embraces the characteristic energies of $\alpha$ emissions from $^{218}$Po (RaA).

4. A method as claimed in claim 3 wherein spill-over of $\alpha$ emissions from Rac' which are detected in said first energy window is corrected for in the calculated actinide count rate value by subtracting a predetermined proportion of the count rate determined in said second energy window from the count rate determined in said first energy window.

5. A method as claimed in claim 4 wherein the $\alpha$ emissions from RaA are compensated for in the calculated actinide count rate value by analysis for the variation with time of the count rate determined in the first energy window, as corrected for said spill over of $\alpha$ emissions from RaC'.

6. A method as claimed in claim 1 wherein air from the region to be monitored is sampled continuously by presenting successive clean surface regions of collecting medium for collection of separated particles thereon during respective collecting periods, and transferring said surface regions to the detecting position after each collecting period.

7. A method as claimed in claim 6 and including the steps of calculating a count value for each successive collected sample corresponding to $\alpha$ emissions from actinide bearing particles in the sample, keeping an aggregate count during a normal working shift period of the total of calculated count values from successive collected samples since the start of the shift period, and producing an alarm signal if the aggregate count exceeds a predetermined maximum value during the shift period.

8. Apparatus for monitoring the airborne radioactivity concentration represented by actinide bearing particles, comprising means to draw a sample stream of air from the region to be monitored, a collection medium at a collecting position, means to separate preferentially by size particles from the stream which are characteristic of actinide bearing particles from particles characteristic of the majority of natural dust particles and to collect said particles characteristic of actinide bearing particles onto the surface of said collecting medium at the collecting position to provide a collected sample of particles, a detector for detecting and providing indications of the relative energy of α radioactive emissions from a sample at a detecting position, means to transfer the collection medium with said sample of particles thereon from the collecting position to the detecting position, and counting and calculating means responsive to said indications from the detector and arranged:

(a) to provide indications of the respective count rates of emissions detected having energies in each of a first energy window embracing the characteristic energies of actinide α emissions and excluding the characteristic energies of α emissions from $^{214}$Po (RaC') and a second energy window embracing said characteristic energies of α emissions from Rac' and excluding said characteristic energies of actinide α emissions;

(b) to determine from said count rate indications the variation with time of at least the count rate for said first energy window for the same collected sample; and (c) to calculate, from said count rate indications and said variation, a value for the count rate for α emissions from actinide bearing particles in the collected sample.

9. Apparatus as claimed in claim 8 wherein said means to separate and collect onto the surface of the collecting medium comprises an inertial impactor arranged to separate by size and impact said particles characteristic of actinide bearing particles onto said surface.

10. Apparatus as claimed in claim 9 wherein said collecting medium is substantially impermeable to air.

11. Apparatus as claimed in claim 10 wherein said surface of said collecting medium is sufficiently hard to prevent particles impacted thereon from penetrating substantially into the medium.

12. Apparatus as claimed in claim 11 wherein the collecting medium is paper having a glazer surface.

13. Apparatus as claimed in claim 12 and including a thin layer of a sticky material provided on the surface of the paper to ensure particles impacting the surface become attached thereto.

14. Apparatus as claimed in claim 13, wherein the collecting medium is formed as an elongate web of material extending parallel to the direction of transfer from the collecting position to the detecting position, and said means to transfer is arranged to move the web lengthwise.

15. Apparatus as claimed in claim 14 and including clamp means operable to clamp respective portions of the web in the collecting and detecting positions and to release said portions to permit the web to move when the portion thereof carrying the sample collected at the collecting position is transferred to the detecting position.

16. Apparatus as claimed in 15 and including a supply roll of said web of material from which the material is drawn during transfers of successive collected samples from the collecting position to the detecting position, said means to transfer including a take-up spool for the web, a motor to drive the take-up spool to draw the web from the supply roll during said transfers, and means controlling the motor to stop drawing further web material for the respective transfer once a length corresponding to the distance between said collecting and detecting positions has been drawn from the supply roll.

17. Apparatus as claimed in claim 16 wherein said means controlling the motor includes a tracking wheel engaging the web to be rotated by movement of the web during a transfer, means responsive to the tracking wheel rotating during a transfer through a predetermined angle corresponding to said length of web, to stop the motor.

18. Apparatus as claimed in claim 17 wherein the circumference of the tracking wheel is equal to an integral number of said lengths.

19. Apparatus as claimed in claim 8 wherein the detector is a silicon surface barrier detector having a detection face.

20. Apparatus as claimed in claim 19 and including clamp means operable to hold said sample of particles on the collection medium at a predetermined proximity to but not touching said detection face for detection of emissions from the sample.

21. Apparatus as claimed in claim 8 wherein said counting and calculating means are arranged such that said first energy window embraces the characteristic energies of α emissions from $^{218}$Po (RaA).

22. Apparatus as claimed in claim 21 wherein said counting and calculating means are arranged to correct, in the calculated actinide count rate value, for spill-over of α emissions from Rac' which are detected in said first energy window, by subtracting a predetermined proportion of the count rate determined in the second energy window from the count rate determined in the first energy window.

23. Apparatus as claimed in claim 22 wherein said counting and calculating means are arranged to compensate, in said calculated actinide count rate value, for the α emissions from RaA, by analysing the variation with time of the count rate determined in the first energy window, as corrected for said spill-over of α emissions from RaC'.

24. Apparatus as claimed in claim 8 and arranged to provide continuous sampling of air from the region to be monitored, successive clean surface regions of collecting medium being presented to said means to separate and collect, for collection thereon of said particles during respective collecting periods, and said means to transfer being operative to transfer said surface regions to the detecting position after said successive collecting periods.

25. Apparatus as claimed in claim 24 wherein said means to transfer is operative to hold each other said surface region at the detecting position for the duration of the collecting period for the next successive surface region at the collecting position.

26. Apparatus as claimed in claim 25 wherein the successive collecting periods are of the same duration which is less than the normal working shift period.

27. Apparatus as claimed in claim 26 wherein each said collecting period is less than one hour.

28. Apparatus as claimed in claim 27 wherein said counting and calculating means is arranged to calculate a count value for each successive collected sample corresponding to α emissions from actinide bearing particles in the sample, and to keep an aggregate count during a normal working shift period of the total of calculated count values from successive collected samples since the start of the shift period, and the apparatus includes alarm means responsive to the aggregate count to produce an alarm signal if the aggregate count exceeds a predetermined maximum value during the shift period.

* * * * *

UNITED STATES PATENT AND TRADEMARK OFFICE
CERTIFICATE OF CORRECTION

PATENT NO. : 4,808,827
DATED : February 28, 1989
INVENTOR(S) : Paul B. Woollam

It is certified that error appears in the above-identified patent and that said Letters Patent is hereby corrected as shown below:

IN THE BACKGROUND OF THE INVENTION

In column 1, line 42, after "forty" please insert --hour--.

In column 1, line 58, please delete "to" and substitute therefor --of--.

In column 3, line 55, please delete "articles" and substitute therefor --article--.

IN THE BRIEF SUMMARY OF THE INVENTION

In column 5, line 16, please delete "Rac'" and substitute therefor --RaC'--.

In column 5, line 23, please delete "Rac'" and substitute therefor --RaC'--.

In column 5, line 26, please delete "Rac'" and substitute therefor --RaC'--.

In column 5, line 65, please delete "Rac'" and substitute therefor --RaC'--.

In column 6, line 2, please delete "Rac'" and substitute therefor --RaC'--.

In column 6, line 15, please delete "Rac'" and substitute therefor --RaC'--.

UNITED STATES PATENT AND TRADEMARK OFFICE
CERTIFICATE OF CORRECTION

PATENT NO. : 4,808,827

DATED : February 28, 1989

INVENTOR(S) : Paul B. Woollam

It is certified that error appears in the above-identified patent and that said Letters Patent is hereby corrected as shown below:

In column 7, line 5, after "stream" please insert --which are characteristic of actinide bearing particles--.

In column 7, line 23, please delete "Rac'" and substitute therefor --RaC'--.

In column 8, line 24, please delete "Rac'" and substitute therefor --RaC'--.

IN THE DETAILED DESCRIPTION

In column 9, line 28, please delete "floor" and substitute therefor --flow--.

In column 11, line 63, please delete "periods" and substitute therefor --period--.

In column 11, line 67, please delete "strings" and substitute therefor --springs--.

In column 12, line 3, please delete "take up" and substitute therefor --take-up--.

In column 12, line 28, please delete "half" and substitute therefor --halt--.

In column 12, line 33, please delete "a" and substitute therefor --$\alpha$--.

UNITED STATES PATENT AND TRADEMARK OFFICE
CERTIFICATE OF CORRECTION

PATENT NO. : 4,808,827
DATED : February 28, 1989
INVENTOR(S) : Paul B. Woollam

It is certified that error appears in the above-identified patent and that said Letters Patent is hereby corrected as shown below:

In column 12, line 43, please delete "amplifier" and substitute therefor --amplified--.

In column 13, line 4, please delete "15" and substitute therefor --13--.

In column 13, line 43, please delete "6.25" and substitute therefor --6.15--.

In column 13, line 50, please delete "Rac'" and substitute therefor --RaC'--.

In column 13, line 64, please delete "Rac'" and substitute therefor --RaC'--.

In column 14, line 5, please delete "Rac'" and substitute therefor --RaC'--.

In column 14, line 7, please delete "Rac'" and substitute therefor --RaC'--.

In column 14, line 10, please delete "Rac'" and substitute therefor --RaC'--.

In column 14, line 26, please delete "Rac'" and substitute therefor --RaC'--.

UNITED STATES PATENT AND TRADEMARK OFFICE
CERTIFICATE OF CORRECTION

PATENT NO. : 4,808,827
DATED : February 28, 1989
INVENTOR(S) : Paul B. Woollam

It is certified that error appears in the above-identified patent and that said Letters Patent is hereby corrected as shown below:

In column 14, line 38, please delete "Rac'" and substitute therefor --RaC'--.

In column 14, line 49, please delete "Rac'" and substitute therefor --RaC'--.

In column 15, line 37, please delete "Rac'" and substitute therefor --RaC'--.

In column 15, line 39, please delete "split" and substitute therefor --spilt--.

In column 16, line 26, please delete "re.g.ion" and substitute therefor --region--.

In column 16, line 52, please delete
"$P= -0.48\alpha_1+1.37\alpha_2+f(0.48\alpha_1-1.37\alpha_2)-B.$" and substitute therefor
--$P= -0.48\alpha_1+1.37\alpha_2+f(0.48\beta_1-1.37\beta_2)-B.$--.

In column 16, line 68, after "Plotting" please insert --the--.

In column 17, line 6, please delete "Rac'" and substitute therefor --RaC'--.

UNITED STATES PATENT AND TRADEMARK OFFICE
CERTIFICATE OF CORRECTION

PATENT NO. : 4,808,827
DATED : February 28, 1989
INVENTOR(S) : Paul B. Woollam

It is certified that error appears in the above-identified patent and that said Letters Patent is hereby corrected as shown below:

In column 17, line 13, please delete "Rac'" and substitute therefor --RaC'--.

In column 17, line 19, please delete "Rac'" and substitute therefor --RaC'--.

In column 18, line 12, please delete "Rac'" and substitute therefor --RaC'--.

In column 18, line 31, please delete "Rac'" and substitute therefor --RaC'--.

In column 19, line 17, please delete "Rac'" and substitute therefor --RaC'--.

In column 20, line 26, please delete "Rac'" and substitute therefor --RaC'--.

Signed and Sealed this

Twenty-ninth Day of October, 1991

Attest:

HARRY F. MANBECK, JR.

*Attesting Officer*  *Commissioner of Patents and Trademarks*